US007842716B2

(12) United States Patent
Serebruany

(10) Patent No.: US 7,842,716 B2
(45) Date of Patent: Nov. 30, 2010

(54) TREATING VASCULAR EVENTS WITH STATINS BY INHIBITING PAR-1 AND PAR-4

(75) Inventor: Victor L. Serebruany, Elicott City, MD (US)

(73) Assignee: HeartDrug Research, LLC, West Friendship, MD (US)

( * ) Notice: Subject to any disclaimer, the term of this patent is extended or adjusted under 35 U.S.C. 154(b) by 1191 days.

(21) Appl. No.: 10/811,563

(22) Filed: Mar. 29, 2004

(65) Prior Publication Data

US 2005/0215618 A1    Sep. 29, 2005

(51) Int. Cl.
| | |
|---|---|
| A61K 31/40 | (2006.01) |
| A61K 31/21 | (2006.01) |
| A61K 31/445 | (2006.01) |
| A61K 31/44 | (2006.01) |
| A01N 43/36 | (2006.01) |
| A01N 37/00 | (2006.01) |

(52) U.S. Cl. .................. 514/423; 514/510; 514/320; 514/354

(58) Field of Classification Search ............... None
See application file for complete search history.

(56) References Cited

U.S. PATENT DOCUMENTS 6,180,660 B1 *  1/2001  Whitney et al. ............. 514/451

OTHER PUBLICATIONS

Gershlick et al. Recent advances: treament of myocardial infarction. BMJ, 316, pp. 280-284, 1998.*
Birnbaum et al. Reduction of infarct size by short-term pretreatment with atorvastatin. Cardiovascular Drugs and Therapy, 17, 25-30, 2003.*
Serebruany VL, et al., Absence of Interaction Between Atorvastatin and Clopidogrel in Prospective Data: The Interaction of Atorvastatin and Clopidogrel (INTERACTION Study). *European Heart Journal*; vol. 24 Suppl: 404 (Mar. 31, 2003).
Serebruany, Victor L., et al., *Thrombosis Res.* 113(3-4): 197-204 (2004).
Saw, J. et al., Lack of Adverse clopidogrel-atorvastatin Clinical Interaction . . . , *Circulation* 108(8):921-4 (2003).
Serebruany, Victor L. et al., Effects of Clopidogrel and aspirin combination . . . , *Am Heart J.* 146(4) 713-20 (2003).
Serebruany, Victor L. et al., *Circulation*, 107(12):1568-1569 (Apr. 1, 2003).
Hebert, PR et al. Cholesterol lowering with statin drugs, risk of stroke, and total mortality. An overview of randomized trials. *JAMA.* 278: 1660-1661 (1997).
Serruys, PW et al. Lescol Intervention Prevention Study (LIPS) Investigators. Fluvastatin for prevention of cardiac events following successful first percutaneous coronary intervention: a randomized controlled trial. *JAMA.* 287: 3215-3222 (2002).
Sotiriou CG, Cheng JW. Beneficial effects of statins in coronary artery disease—beyond lowering cholesterol. *Ann Pharmacother.* 34:1432-1439 (2000).

Takemolot, Masao et al., Pleiotropic effects of 3-hydroxy-3-methylglutaryl coenzyme a reductase inhibitors. *Arterioscler Thromb Vase Biol.*; 21:1712-1719 (2001).
Sanguigni V. et al., Increased superoxide anion production by platelets in hypercholesterolemic patients. *Thromb Haemost.* 87:796-801 (2002).
Vu T-K.H., et al. Molecular cloning of a functional thrombin receptor reveals a novel proteolytic mechanism of receptor activation. *Cell.* 64: 1057-1068 (1991).
Kahn ML, et al. Protease activated receptors 1 and 4 mediate activation of human platelets by thrombin. *Clin Invest.* 103: 879-887 (1999).
Brass LF, et al. Changes in the structure and function of the human thrombin receptor during receptor activation, internalization, and recycling. *J Biol Chem.* 269: 2934-2952 (1994).
Puccetti L, et al. Effect of diet and treatment with statins on platelet-dependent thrombin generation in hypercholesterolemic subjects. *Nutr Metab Cardiovasc Dis.* 11: 378-387 (2001).
Savi P, et al. Identification and biological activity of the active metabolite of clopidogrel. *Thromb Haemost.* 84:891-896 (2000).
Williams D, Feely J. Pharmacokinetic-pharmacodynamic drug interactions with HMG-CoA reductase inhibitors. *Clin Pharmacokinet.* 41:343-370 (2002).
Clarke TA, Waskell LA. The metabolism of clopidogrel is catalyzed by human cytochrome P450 3A and is inhibited by atorvastatin. *Drug Metabol Dispos.* 31: 53-59 (2002).
Chambers RC, et al., Thrombin is a potent inducer of connective tissue growth factor production via proteolytic activation of protease-activated receptor-1. *J Biol Chem.* Nov. 10;275(45):35584-91 (2000).
Phillips DR. Thrombin interaction with human platelets: potentiation of thrombin-induced aggregation and release by inactivated thrombin. *Thromb Diathesis Haemorrhag.* 32:207-215 (1974).
Pilcher BK, Thrombin stimulates fibroblast-mediated collagen lattice contraction by its proteolytically activated receptor. *Exp Cell Res.* 211:368-373 (1994).
Sower LE, Froelich CJ, Carney DH, Fenton JW II, Klimpel GR. Thrombin induces IL-6 production in fibroblasts and epithelial cells: evidence for the involvement of the seven-transmembrane domain (STD) receptor for -thrombin. *J Immunol.* 155:895-901 (1995).
Rabiet M, Plantier J, Rival Y, Genoux Y, Lampugnani M, Del Mar EG. Thrombin-induced increase in endothelial permeability is associated with changes in cell-to-cell junction organization. *Arterioscler Thromb Vasc Biol.* 16:488-496 (1996).
Kinlough-Rathbone RL, Rand ML, Packham MA. Rabbit and rat platelets do not respond to thrombin receptor peptides that activate human platelets. *Blood.* 82:103-106 (1993).

(Continued)

*Primary Examiner*—Brandon J Fetterolf
*Assistant Examiner*—Anna Pagonakis
(74) *Attorney, Agent, or Firm*—Antoinette G Giugliano PC

(57) ABSTRACT

The present invention relates to new methods for treating and/or preventing vascular events by inhibiting G-coupled Protease Activating Receptor (PAR)-1 and/or PAR-4 with the administration of statins. In one embodiment, individuals who are at risk for vascular events, but have cholesterol levels (e.g., total cholesterol or Low Density Lipoprotein) in normal ranges, are treated with statins.

1 Claim, No Drawings

OTHER PUBLICATIONS

Henriksen RA, Samokhin GP, Tracy PB. Thrombin-induced thromboxane synthesis by human platelets. Properties of anion binding exosite I-independent receptor. *Arterioscler Thromb Vasc Biol.* 17(12): 3519-26 (1997).

Weksler, B. B., C. W. Ley, and E. A. Jaffe. Stimulation of endothelial cell prostacyclin production by thrombin, trypsin, and the ionophore A23187. *J. Clin. Invest.* 62: 923-930 (1978).

Sugama, Y., C. Tiruppathi, K. Janakidevi, T. T. Andersen, J. W. Fenton II, and A. B. Malik. Thrombin-induced expression of endothelial P-selectin and intercellular adhesion molecule-1: a mechanism for stabilizing neutrophil adhesion. *J. Cell Biol.* 119: 935-944 (1992).

Tannous, M. et al. Atorvastatin increases ecNOS levels in human platelets of hyperlipidemic subjects. *Thromb Haemost.* 82:1390-1394 (1999).

Puccetti, L. et al. Time-dependent effect of statins on platelet function in hypercholesterolaemia. *Eur J Clin Invest.* 32: 901-908 (2002).

De Candia E, Hall SW, Rutella S, Landolfi R, Andrews RK, De Cristofaro R. Binding of thrombin to glycoprotein Ib accelerates the hydrolysis of Par-1 on intact platelets. *J Biol Chem.* 276(7):4692-8 (2001).

Kahn, M. L., Diacovo, T. G., Bainton, D. F., Lanza, F., Trejo, J. & Coughlin, S. R. *Blood* 94, 4112-4121 (1999).

Ramakrishnan, V., Reeves, P. S., DeGuzman, F., Deshpande, U., Ministri-Madrid, K., DuBridge, R. B. & Phillips, D. R. *Proc. Natl. Acad. Sci. USA* 96, 13336-13341 (1999).

Ramakrishnan, V., DeGuzman, F., Bao, M., Hall, S. W., Leung, L. L. & Phillips, D. R. *Proc. Nat. Acad. Sci. USA* 98, 1823-1828 (2001).

Roth GJ, "A new "kid" on the platelet thrombin receptor "block": glycoprotein Ib-IX-V" *Proc Natl Acad Sci U S A* 98(4):1330-1 (2001).

Neubauer, Horst, et al., *European Heart J.* 24(19):1744 (Oct. 2003).

Saucedo, Jorge F., et al., *Circulation* 108 (17 supplement):IV-579 (Oct. 28, 2003).

Muller, Iris, et al., *Circulation* 108(18):2195-2197 (Nov. 4, 2003).

Olvotti, L., et al. High doses of atorvastatin do not affect activity of prothrombinase in patients with acute coronary syndromes. *Blood Coag Fibrin.* 13:315-322 (2002).

Gaddam, V., et al, *J. Cardiovascular Pharm & Therap*, 7(4):247-253 (Oct. 2002).

Puccetti, L. et al., *European J of Clinical Investig.*, 32(12):901-908 (Dec. 2002).

Laufs, U et al., Atorvastatin upregulates type III nitric oxide synthase in thrombocytes, decreases platelet activation, and protects from cerebral ischemia in normocholesterolemic mice. *Stroke* 10:2442-2449 (2000).

Law, Wei C.., et al., *Circulation*, 102(18 supplement):II.429 (Oct. 31, 2000).

Lau, WC, et al *Circulation*, 107(1):32-37 (2003).

Serebrauny, Victor L., MD, PhD. Absence of Interaction Between Atorvastatin or Other Statins and Clopidogrel. *Archives of Internal Medicine.* 2004; 164; 2051-2057.

\* cited by examiner

TREATING VASCULAR EVENTS WITH STATINS BY INHIBITING PAR-1 AND PAR-4

BACKGROUND OF THE INVENTION

Coronary Heart Disease (CHD) is one of the most common diagnoses of hospital patients in the United States, with over five million cases occurring yearly. High levels of bad cholesterol (Low Density Lipoprotein (LDL-C)), total cholesterol (Total-C) or triglycerides are often associated with increased incidence of CHD, stroke and other vascular events. These patients are frequently treated with lipid lowering drugs, such as statins. In certain aspects, the biological mechanisms of these statins remain unclear.

However, many individuals exist who have normal levels of bad cholesterol, total cholesterol, or triglycerides, but still suffer from or are at risk for such vascular events. These vascular events pose serious problems to patients and the physicians who treat them. Physicians continue to search for better preventative and/or curative treatments for vascular diseases.

Hence, a need exists for new and improved treatment options for individuals who have vascular diseases, particularly for those individuals having cholesterol levels in normal ranges. Additionally, a need exists to determine the mechanisms underlying vascular disorders, so that better therapies which target these patient types can be developed.

SUMMARY OF THE INVENTION

The present invention is based on the surprising discovery that statins, a cholesterol lowering drug, inhibit a G-coupled Protease Activating Receptor (PAR)-1 and/or PAR-4 (e.g., platelet PAR-1 and/or platelet PAR-4). This newly discovered mechanism has led to new methods for treating individuals who have a vascular disease or who are at risk for developing such a disease.

Accordingly, the present invention relates to methods for treating a vascular disorder in an individual by assessing the levels of PAR-1, PAR-4, or both. When the individual has an elevated level of PAR-1, PAR-4 or both, then the method includes administering to the individual an effective amount of a statin to reduce the levels of PAR-1, PAR-4 or both.

The present invention also embodies methods for reducing a PAR-1 level, a PAR-4 level, or both in an individual, by selecting an individual having an elevated PAR-1 level, an elevated PAR-4 level, or both; and administering to the individual an effective amount of a statin to reduce the PAR-1 level, the PAR-4 level or both. In one embodiment, the present invention pertains to selecting individuals that also have total-C levels, LDL-C levels or triglyceride levels that are not considered to be high (e.g., in the normal or low ranges). More specifically, the present invention includes individuals with a Total-C level of less than about 200 mg/dL (e.g, normal range is considered to be between about 60 mg/dL and about 199 mg/dL). Similarly, the present invention further embodies individuals having LDL-C levels that are less than about 130 mg/dL (e.g., normal range is between about 85 mg/dL and about 129 mg/dL). Yet, the present invention can also be practiced on individuals having triglyceride levels of less than 150 mg/dL (e.g., a normal range is between about 30 mg/dL and about 149 mg/dL).

As described herein, PAR-1, PAR-4 or both can be reduced by at least about 10% (e.g., 20%, 30%, 40%, 50%, 60%, 70%, 80%, or 90%), as compared to a control. Examples of statins include, but are not limited to, atorvastatin, pravastatin, fluvastatin, cerivastatin, lovastatin, simvastatin, rosuvastatin, pitavastatin, and metabolites thereof. Effective amounts of statins include oral administration in an amount between about 5 mg and about 250 mg per day, as further described herein.

The present invention, in another embodiment, relates to methods for treating an individual with a vascular disorder or preventing a vascular disorder in an individual who is as risk for developing one. This method is performed by selecting an individual that has a vascular disorder; and a Total-C level of less than 200 mg/dL, or a LDL-C level of less than 130 mg/dL, or both; and administering to the individual an effective amount of a statin to inhibit PAR-1, PAR-4 or both. Vascular disorders include, but are not limited to, myocardial infarction, angina, stroke, pulmonary embolism, transient ischemic attack, deep vein thrombosis, thrombotic re-occlusion subsequent to a coronary intervention procedure, heart surgery or vascular surgery, peripheral vascular thrombosis, Syndrome X, heart failure and a disorder in which a narrowing of at least one coronary artery occurs. Statins are administered, and PAR-1 and/or PAR-4 are reduced, as further described herein.

When statins inhibit PAR-1 and/or PAR-4, statins, in turn, reduce or prevent thrombin generation. Consequently, the present invention includes methods for reducing or preventing thrombin generation in an individual. The method involves selecting an individual that has elevated PAR-1, PAR-4 or both; or selecting an individual that has a vascular disorder; and a Total-C level of less than 200 mg/dL, or a LDL-C level of less than 130 mg/dL, or both. After the individual is selected, the method includes administering to the individual an effective amount of a statin to inhibit PAR-1, PAR-4 or both. These steps reduce the amount of thrombin generation, as compared to the amount of thrombin generation prior to administration.

Yet an additional embodiment includes methods for inhibiting PAR-1, PAR-4 or both in a cell, by contacting the cell with an effective amount of a statin. This process can occur in vivo, in vitro or ex vivo, as further described herein.

DETAILED DESCRIPTION OF THE INVENTION

The present invention relates to a new treatment for vascular disorders (e.g., heart disease and stroke). In particular, the present invention is based on the unexpected discovery that certain receptors, known as G-coupled Protease Activating Receptor (PAR)-1 and PAR-4, are inhibited by a statin, a lipid-lowering drug. Hence, the present invention pertains to treating or preventing vascular disorders by administering a statin to inhibit PAR-1, PAR-4 or both.

Prior to the invention, it had been understood that statins can be used to lower cholesterol levels by inhibiting HMG-CoA (3-hydroxy-3-methylglutaryl-coenzyme A) reductase, an enzyme thought to facilitate the synthesis cholesterol. However, two surprising aspects of the invention exists. The first aspect is that statins, in addition to inhibiting HMG-CoA reductase, also inhibit PAR-1 and/or PAR-4 receptors. As such, patients who have cholesterol levels in normal ranges, but are at risk for heart disease or stroke (e.g., vascular events), can effectively be treated with statins. Second, inhibiting PAR-1, PAR-4 or both with statins actually reduce the incidence of vascular events.

The present invention pertains to methods for preventing or treating an individual at risk for a (e.g., one or more) vascular event, disease or disorder. The data described herein unexpectedly show that inhibiting PAR-1 and/or PAR-4 reduce the severity of or prevent vascular events. Prevention of a vascular event, condition, disease or disorder (e.g., thrombotic event, condition, disease or disorder) refers to delaying or suppressing the onset of the vascular disorder, or one or more of its symptoms. To treat an individual at risk for a vascular disorder means to alleviate, ameliorate or reduce the severity of one or more of its symptoms.

Two phases of thrombotic events e.g., cardiovascular and/or cerebrovascular events, can exist: an ischemic stage and a necrotic stage. A patient can suffer from ischemia in which a decrease of blood flow can occur. This decrease in blood flow causes a decrease in tissue oxygenation. After prolonged ischemia, the tissue can undergo necrosis which is death of the tissue. Therefore, patients who are at risk for a vascular event can exhibit elevated levels of ischemic markers and/or necrosis markers.

An individual at risk for a vascular disorder refers to an individual with a history of vascular disease, an individual experiencing at least one symptom of the disorder, an individual having known risk factors (e.g., gender, weight) associated with or caused by the vascular disorder, an individual undergoing a vascular procedure, or an individual who has tested positive for a vascular condition using a diagnostic test (e.g., electrocardiogram, cardiac catheterization, stress test, ultrasound techniques, laboratory tests).

As described above, an embodiment of the invention includes treating individuals who are at risk for vascular events because they manifest at least one symptom indicative of a vascular disorder/event. Symptoms that are indicative of a coronary-related vascular event, for example, include chest pain, abnormal electrocardiograms, elevated levels of ischemic markers, necrosis markers, or thrombin/fibrin generation markers. Such markers include, but are not limited to, Creatine Kinase with Muscle and/or Brain subunits (CKMB), D-Dimer, F1.2, thrombin anti-thrombin (TAT), soluble fibrin monomer (SFM), fibrin peptide A (FPA), myoglobin, thrombin precursor protein (TPP), platelet monocyte aggregate (PMA) and troponin. Individuals who are at risk also include those having a history of a vascular event (e.g. disorder), including Coronary Heart Disease (CHD), stroke, or Transient Ischemic Attacks (TIAs). A history of CHD can include, for example, a history of MI, coronary revascularization procedure, angina with ischemic changes, or a positive coronary angiogram (e.g., showing greater than about 50% stenosis of at least one major coronary artery).

The present invention also relates to methods for reducing the occurrence or severity of a vascular disorder in a patient who is at risk for such a disorder. Reducing the occurrence of a vascular disorder (e.g., a cardiovascular and/or cerebrovascular disorder) refers to reducing the probability that a patient will develop the disorder, or delaying the onset of the disorder. Reducing the severity of a vascular disorder refers to a reduction in the degree of at least one symptom of the disorder. The present invention embodies methods for preventing the onset of a vascular disorder in an individual having less than about a 130 mg/dL LDL-C level, about a 200 mg/dL of Total-C or both by administering a statin.

A vascular disorder is a event, disease or disorder that involves a thrombosis (e.g., a thrombotic event) or a narrowing of a blood vessel. A vascular disorder/event occurs, for example, when a clot forms and lodges within a blood vessel. The blockage can fully block or partially block the blood vessel causing a vascular disorder. Thrombin generation refers to the activation, expression or up-regulation of thrombin, which is involved in clot formation and an inductor of platelet activation. The amount of thrombin generation can be measured or assessed by certain markers known in the art. Examples of such thrombin generation markers include fibrinopeptide A, prothrombin fragments 1+2, and thrombin-antithrombin-III complexes.

Thrombin is a potent serine protease that plays a central role in homeostasis following tissue injury by converting soluble plasma fibrinogen into an insoluble fibrin clot and by promoting platelet aggregation. In addition to these procoagulant effects, thrombin also influences a number of cellular responses that play important roles in subsequent inflammatory and tissue repair processes. Thrombin influences the recruitment and trafficking of inflammatory cells and is a potent mitogen for a number of cell types, including endothelial cells, fibroblasts, and smooth muscle cells. Thrombin also promotes the production and secretion of extracellular matrix proteins and influences connective tissue remodeling processes. There is increasing in vivo evidence that the pro-inflammatory and pro-fibrotic effects of thrombin play an important role in both normal tissue and vascular repair, as well as in a number of pathological conditions associated with acute or persistent activation of the coagulation cascade, including restenosis and neointima formation following vascular injury, atherosclerosis, pulmonary fibrosis, and glomerulonephritis.

It has been determined that most of the cellular effects elicited by thrombin are mediated via a family of expressed PAR-1 receptors that are activated by limited proteolytic cleavage of the N-terminal extracellular domain. The newly generated N-terminus acts as a tethered ligand and interacts intramolecularly with the body of the receptor to initiate subsequent cell signaling events. When PAR-1 or PAR-4 is proteolytically cleaved, the new amino terminus functions as a tethered ligand to initiate signal transduction, and peptides derived from the new amino terminus, thrombin receptor agonist peptides, function as agonists for the uncleaved receptor. As defined herein, thrombotic events include those involving thrombin formation. In one embodiment, the present invention relates to methods of preventing or treating thrombin formation in individuals, as described herein, by administering a statin.

Vascular events, diseases or disorders include cardiovascular diseases (e.g., coronary heart disease, myocardial infarction, angina or a disease in which a narrowing of a blood vessel occurs in at least one major artery), cerebrovascular diseases (e.g., stroke or transient ischemic attacks), vascular procedures (e.g., thrombotic re-occlusion subsequent to a coronary intervention procedure, heart or vascular surgery) or any other thrombotic event (e.g., pulmonary embolism, deep vein thrombosis or peripheral vascular thrombosis). Vascular disorders also include Syndrome X, which is a disease that is associated with unidentified chest pain. Vascular disorders include those in which at least one major coronary artery exhibits greater than 50% stenosis.

Also, administering a statin can result in a reduction of recurrent vascular events (e.g., cardiovascular and/or cerebrovascular events). Use of the methods described herein results in a reduction of at least about 10% (e.g., 15%, 20%, 25%) in the number of recurrent heart attacks, cardiac deaths and/or strokes.

In one aspect, the present invention involves assessing the PAR-1 level, the PAR-4 level, or both to determine if the either or both levels are elevated. Individuals with elevated PAR-1 and/or the PAR-4 levels can be at risk for vascular events. Individuals can have other risk factors for vascular events, as further described herein. Administration of statins inhibit PAR-1 and/or PAR-4, and levels of PAR-1 and/or PAR-4 are reduced, as compared to level(s) prior to administration of the statin. Controls and assessment of PAR-1 and/or PAR-4 are further described herein. Statin administration prevents, reduces or treats the vascular disorder.

A lipid profile is made up of a number of items including, but not limited to, High Density Lipoprotein-Cholesterol (HDL-C), Low Density Lipoprotein-Cholesterol (LDL-C), triglycerides, and total Cholesterol (Total-C). Lipoproteins are complexes which contain both a lipid and protein. Most of the lipids in plasma are present as lipoproteins and are transported as such. Lipoproteins are characterized by their flotation constants (e.g., densities). Various classes of lipoproteins exist and include HDLs and LDLs. LDLs are particularly rich in cholesterol esters.

Levels of cholesterol that are considered normal can vary and depend on factors such as the individual's health history, the number of risk factors the individual has, etc. The National Cholesterol Education Program (NCEP) Guidelines state that a Total-C of greater than or equal to 200 mg/dL, and a LDL-C of greater than or equal to 130 mg/dL are considered borderline high. In one embodiment, the present invention relates to administering a (e.g., one or more) statin to an individual with Total-C and/or LDL-C level(s) that are not considered to be high or borderline high (e.g., individuals with levels in normal ranges). For example, a normal range of Total-C is considered to be between about 60 mg/dL and about 199 mg/dL, and LDL-C is between about 85 mg/dL and about 129 mg/dL. As such, the present invention embodies administering a statin to an individual having a Total-C of less than about 200 mg/dL (e.g., between about 60 mg/dL and about 199 mg/dL) and/or a LDL-C of less than about 130 mg/dL (e.g., between about 85 mg/dL and 129 mg/dL). Additionally, the present invention embodies administering a statin to an individual with triglyceride levels in normal ranges, e.g., administering a statin to an individual with a triglyceride level of less than 150 mg/dL (e.g., between about 30 mg/dL and about 149 mg/dL).

One embodiment of the invention includes administering a statin to an individual having a Total-C and/or a LDL-C level in the upper end of the normal range. For example, an individual having a LDL-C level in the range of about 100 mg/dL and about 129 mg/dL is considered to be in the normal range, but not optimal. Similarly, an individual with a Total-C in a range from about 170 mg/dL to about 199 mg/dL are also considered to be normal, but not optimal. As such, individuals at risk for a vascular event, as described herein, and have levels of LDL-C or Total-C in the upper portion of the normal range can benefit from the invention. Hence, in one embodiment, the present invention relates to administering a statin to an individual with a LDL-C level of between about 100 mg/dL and about 129 mg/dL, and/or a Total-C level of about 170 mg/dL and about 199 mg/dL. Similarly, triglyceride levels that are on the upper end of the normal range include levels between about 100 mg/dL and about 149 mg/dL. The invention therefore embodies administering a statin to an individual at risk for a vascular event wherein the individual has a triglyceride level between about 100 mg/dL and about 149 mg/dL.

Lipoproteins levels and triglyceride levels are measured and assessed using routine methods known in the art. Commercially available kits and assays can be used to evaluate the levels of Total-C, HDL-C, LDL-C and triglycerides.

The present invention relates to methods of reducing or preventing vascular events by administering to an individual an effective amount of a statin. The term, "statin" refers to a (e.g., one or more) compound or metabolite thereof that inhibits HMG-CoA (3-hydroxy-3-methylglutaryl-coenzyme A) reductase, an enzyme thought to facilitate the synthesis cholesterol. More particularly, statins inhibit the conversion of HMG-CoA reductase to mevalonate, a precursor of sterols, including cholesterol. Since the enzyme used to make cholesterol is blocked by the statin, then less cholesterol is made. Cholesterol and triglycerides circulate in the bloodstream as part of lipoprotein complexes. Hence, statins generally lower lipids in this way. Additionally and more importantly, the data described herein demonstrate that statins also block or inhibit PAR-1, PAR-4, or both, thereby reducing or preventing vascular events.

Examples of statins are atorvastatin Atorvastatin Calcium, marketed under the trademark LIPITOR® brand drug by Pfizer, Inc.), pravastatin (e.g., Pravastatin Calcium marketed under the trademark PRAVACHOL® brand drug by Bristol-Myers Squibb), fluvastatin (e.g., Fluvastatin Sodium marketed under the trademark LESCOL® brand drug by Novartis), cerivastatin (e.g., Cerivastatin Sodium marketed under the trademark BAYCOL® brand drug by Bayer Corporation), lovastatin (e.g., Lovastatin marketed under the trademark MEVACOR® brand drug by Merck & Co., Inc.), simvastatin (e.g., Simvastatin marketed under the trademark ZOCOR® brand drug by Merck & Co., Inc.), rosuvastatin (e.g., Rosuvastatin Calcium marketed under the trademark CRESTCOR® brand drug by AstraZeneca, Inc.), pitavastatin (Nissan/Sankyo's nisvastatin (NK-104) or itavastatin), and metabolites thereof. The present invention encompasses statins that are currently used, or those later discovered or formulated. Statins include biologically active portions, groups or fragments of the statin that can inhibit PAR-1 or PAR-4.

Methods of making statins or isolating statins are known in the art. Statins can be make synthetically, or isolated from a bacteria (e.g., *Aspergillus terreus*). Methods of making statins, their chemical formulas and their properties are described, for example, in U.S. Pat. Nos. 3,983,140 (e.g., mevastatin); 4,231,938 (e.g., lovastatin); 4,346,227 (e.g., pravastatin); 4,448,784 (e.g., simvastatin); 4,450,171 (e.g., simvastatin); 5,354,772 (e.g., fluvastatin); 5,006,530 (e.g., cerivastatin); 5,177,080 (e.g., cerivastatin); 4,681,893 (e.g., atorvastatin); 5,273,995 (e.g., atorvastatin); 5,385,929 (e.g., atorvastatin); 5,686,104 (e.g., atorvastatin); 5,260,440 (e.g., rosuvastatin); and 5,011,930 (e.g., pitavastatin).

One aspect of the invention, as described herein, includes administering a statin along with at least one other compound or composition that is used for treating the vascular condition (a "vascular treating compound"). For an individual with a cardiovascular disease, the statin can be administered together with aspirin, heparin, an ADP inhibitor or antagonist (e.g., thienopyridine, such as ticlopidine hydrochloride (marketed under the trademark TICLID® brand drug from Roche Laboratories) or clopidogrel bisulfate (marketed under the trademark PRAVIX® brand drug from Bristol-Myers Squibb and Sanofi), GPIIb/IIIa inhibitors (marketed under the trademark REOPRO® brand drug from Centocor, Inc.; INTEGRILIN® brand drug from Millennium Pharmaceutical, Inc.; AGGRASTAT® brand drug from Gilford Pharmaceutical) or another statin. Individuals with cerebrovascular diseases, for example, can receive a statin together with TICLID® brand drug or PRAVIX® brand drug or aspirin.

The present invention involves inhibiting PAR-1, PAR-4, or both. To determine if PAR-1, PAR-4, or both are inhibited, one can assess or quantify these receptors. PAR-1 and/or PAR-4 can be measured to determine whether an individual has elevated PAR-1 and/or PAR-4 levels, which would indicate that treatment with a statin is needed. In some embodiments, the present invention includes a specific step of assessing or measuring PAR-1, PAR-4, or both. Elevated PAR-1 and/or PAR-4 levels depend on the type of antibody used, e.g.

greater than about 20 for the WEDE-15 antibody and about 40 for the SPAN-12 antibody (in log mean fluorescence).

The phrase "PAR receptors" refers to PAR-1 and/or PAR-4 receptors. "PAR receptor" refers to PAR-1 or PAR-4. In certain embodiments, the invention refers to PAR-1 and/or PAR-4 receptors on the platelet.

A reduction in the PAR-1 and/or PAR-4 levels (e.g., platelet PAR-1 and/or platelet PAR-4) refers to a decrease in or an absence of one or both receptors, as compared to levels prior to administration or as compared to a control, as further described herein. Levels of one or both receptors can be decreased or reduced by at least about 10% (e.g., 20%, 30%, 40%, 50%, 60%, 70%, 80%, or 90%), as compared to the level just prior to administration. Hence, one can measure the presence, absence or level of one or both of these receptors, and compare the result against a control. For example, one can obtain a suitable sample and compare the level of one or both of the receptors from previous time points (e.g., prior to administration of the statin or during the onset of a vascular event, disease or disorder). PAR-1 and/or PAR-4 levels decrease after administration of the statin, as compared to the level during the onset of the vascular event. One can also measure PAR-1 and/or PAR-4 levels in an individual prior to the onset of a vascular event (e.g., in a resting state or during a check-up), to determine the individual's baseline. Accordingly, administration of a statin after the onset of a vascular disease decreases the levels of PAR-1 and/or PAR-4 levels, as compared to those levels during the onset of the vascular disease, to reduce the level(s) so that they are closer to baseline (e.g., above, at or below baseline, but less than level(s) during the onset of the vascular disease).

The PAR-1 and/or PAR-4 levels assessed can also be compared to a standard or control obtained from normal individuals. In one example, PAR-1 and/or PAR-4 levels can be assessed in a population of healthy individuals or individuals who have not had a vascular event, disease or disorder. Such levels are referred to as a "negative control." Conversely, PAR-1 and/or PAR-4 levels can also be obtained from a pool of individuals who are undergoing a vascular event, disease or disorder, e.g., a "positive control." After administration of a statin, the level of PAR-1, PAR-4 or both decreases; the level(s) get closer to the level of the negative control, and farther from the positive control. The PAR-1 and/or PAR-4 levels decrease as compared to the levels during the onset of the vascular event, disease or disorder. Hence, the methods of the present invention include reducing or inhibiting PAR-1 and/or PAR-4 levels, with administration of a statin, wherein PAR-1 and/or PAR-4 levels are reduced or decreased, as compared to those levels during the occurrence of the vascular event, disease or disorder, or immediately prior to the administration of a statin.

In another embodiment, the present invention relates preventing the onset of a vascular event, disease or disorder. An effective amount of at least one statin can be administered to prevent PAR-1 and/or PAR-4 levels from increasing, or lessen PAR-1 and/or PAR-4 levels which would otherwise remain elevated without statin administration. For example, an individual who is a risk for a vascular event, disease or condition can take a statin on a daily basis (or every other day), to prevent PAR-1 and/or PAR-4 levels from increasing as compared to a control or baseline. Baseline levels of the activation state can be obtained prior to and/or during the course of administration of a statin. The PAR-1 and/or PAR-4 levels can stay the same, or can even decrease. Similarly, PAR-1 and/or PAR-4 levels can be compared to a negative or positive control, wherein upon administration of statin, the levels are closer to the negative control, than the positive control. However measured, the PAR-1 and/or PAR-4 levels are prevented from increasing, thereby preventing the occurrence of a vascular event, disease or disorder.

The present invention also relates to reducing or inhibiting PAR-1 and/or PAR-4 by contacting the platelets with a statin or metabolite thereof. This embodiment of the invention can be carried out in vivo, in vitro or ex vivo. The method reduces PAR-1 and/or PAR-4 levels, as compared to the level prior to contact of the statin or a metabolite thereof with the platelets.

Immunological Assessment of PAR-1 and PAR-4

Several suitable assays exist that measure the PAR receptors. Suitable assays encompass immunological methods, such as radioimmunoassay, flow cytometry, enzyme-linked immunosorbent assays (ELISA), chemiluminescence assays, and assessment with a volumetric capillary cytometry system. Any method now known in the art or developed later can be used for measuring the PAR receptors.

The assays utilize antibodies reactive with the PAR receptors, portions thereof or functional fragments thereof. The terms polyclonal and monoclonal refer to the degree of homogeneity of an antibody preparation, and are not intended to be limited to particular methods of production.

In several of the embodiments, immunological techniques detect PAR receptor levels by means of an anti-PAR antibody (i.e., one or more antibodies). The phrase "anti-PAR receptor antibody" includes monoclonal (MoAbs) antibodies, polyclonal antibodies, and/or mixtures thereof. For example, these immunological techniques can utilize mixtures or a cocktail of polyclonal and/or monoclonal antibodies.

Anti-PAR antibodies can be raised against an appropriate immunogen, such as isolated and/or recombinant PAR receptors or portion thereof (including synthetic molecules, such as synthetic peptides). One can also raise antibodies against a host cell which expresses a recombinant PAR receptors. Additionally, cells expressing a recombinant PAR receptors, such as transfected cells, can be used as immunogens or in a screen for antibody which binds receptor. Examples of PAR receptor antibodies are WEDE-15 MoAbs (PAR-1 and PAR-4) and SPAN-12 MoAbs (PAR-1 and PAR-4).

Techniques known in the art can be employed to prepare an immunizing antigen and to produce polyclonal or monoclonal antibodies. The art contains a variety of these methods (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest and, preferably, an adjuvant provide the antibody producing cell (cells from the spleen or lymph nodes). Selective culture conditions isolate antibody producing hybridoma cells while limiting dilution techniques produce them. One can use suitable assays such as ELISA to select antibody producing cells with the desired specificity.

Other suitable methods can be employed to produce or isolate antibodies of the requisite specificity. Examples of other methods include selecting recombinant antibody from a library or relying upon immunization of transgenic animals such as mice which are capable of producing a full repertoire of human antibodies (see e.g., Jakobovits et al., *Proc. Natl. Acad. Sci. USA*, 90: 2551-2555 (1993); Jakobovits et al., Nature, 362: 255-258 (1993); Lonberg et al., U.S. Pat. No. 5,545,806; Surani et al., U.S. Pat. No. 5,545,807).

Immunological assays or techniques can be employed to determine the presence, absence or level of PAR receptors in a biological sample. In determining the amounts of a membrane bound and/or soluble PAR receptors, an assay generally includes combining the sample to be tested with an antibody having specificity for one or both of the PAR receptors, under conditions suitable for formation of a complex between antibody and the PAR receptor(s), and detecting or measuring (directly or indirectly) the formation of a complex.

A sample can be obtained and prepared by a method suitable for the particular sample (e.g., whole blood, platelet rich plasma), and select the assay format. For example, suitable methods for whole blood collection are venipuncture or obtaining blood from an in-dwelling arterial line. The container into which one deposits the blood can contain an anticoagulant such as CACD-A, heparin, or EDTA.

One or more PAR receptors can be measured in a sample with or without platelets. To measure a soluble form of the PAR receptors, the platelets are removed from the sample. A sample (e.g., blood) is collected, and platelets are removed (partially or completely) from the sample, for example, by preparation of serum or plasma (e.g., isolation of platelet poor plasma). Samples are processed to remove platelets within a time suitable to reduce artificial increases in soluble PAR receptors. Initiation of such processing within about one hour, and preferably immediately, is desirable. Samples can be further processed as appropriate (e.g., by dilution with assay buffer). Additionally, one can add a reagent which stabilizes and prevents in vitro platelet activation. Examples of these stabilizing reagents are apyrase and $PGE_1$.

Methods of combining sample and antibody, and methods of detecting complex formation are also selected to be compatible with the assay format. Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, CY5, APC, chemiluminescent labels such as luciferase, radioisotope labels such as $^{32}P$, $^{125}I$, $^{131}I$, enzyme labels such as horseradish peroxidase, and alkaline phosphatase, $\beta$-galactosidase, biotin, avidin, spin labels and the like. The detection of antibodies in a complex can also be done immunologically with a second antibody which is then detected.

Flow Cytometry:

One method for assessing PAR receptor levels is flow cytometry. Methods of flow cytometry for measuring platelets or PAR receptors are known in the art. (Shattil, Sanford J, et al. "Detection of Activated Platelets in Whole Blood using Activation-Dependent Monoclonal Antibodies and Flow Cytometry," *Blood*, Vol. 70, No 1 (July), 1987: pp 307-315; Scharf, Rudiger E., et al., "Activation of Platelets in Blood Perfusing Angioplasty-damaged Coronary Arteries, Flow Cytometric Detection," *Arteriosclerosis and Thrombosis*, Vol 12, No 12 (December), 1992: pp 1475-1487.

For example, an assessment of one or more PAR receptors can be done. A sample comprising platelets is obtained from an individual. The sample is contacted with an antibody having specificity for one or both PAR receptors under conditions suitable for formation of a complex between an antibody and the PAR receptor(s) expressed. A fluorescent label is used to detect the complex formation, either directly or indirectly. The in vivo affect of a statin is assessed by obtaining samples at particular time points (e.g., a baseline, during a vascular event, after administration of a statin, etc.), as described herein, and measuring the presence, absence, or level one or more PAR receptors.

For ex vivo assessment of the statins effect on a PAR receptor, a level of a PAR receptor can be assessed by flow cytometry by first obtaining a sample that comprises platelets and then contacting the sample with a platelet activation agonist, such as phorbol myristate acetate (PMA), ADP (adenosine diphosphate), thrombin, collagen, and/or TRAP (thrombin receptor activating peptide), under conditions suitable for activation of platelets in the sample. The sample is in contact with the agonist preferably for a period of time effective to maximally activate the platelets. The sample is then subjected to a statin at particular concentrations. Then one contacts the samples with a composition that comprises an anti-PAR antibody e.g., having a fluorescent label, preferably in an amount in excess of that required to bind the PAR receptor expressed on the platelets, under conditions suitable for the formation of labeled complexes between the anti-PAR antibody and activated platelets. Then the formation of the complex in the sample is assessed (e.g., detected or measured).

The sample can be divided to form controls. For example, a portion of the sample can be maximally activated and not contacted with a statin. Also, one can obtain a portion of the sample and not expose it to a platelet activation agonist, nor the statin to determine a baseline level of the PAR receptors. See Exemplification for detailed description of the flow cytometry methods. This ex vivo method is not limited to flow cytometry, but can also be used in other methods for assessing PAR receptor levels. Receptor expression is presented as Log mean fluorescence intensity.

Radioimmunoassay:

In addition to using flow cytometry to measure a PAR receptor, a radioimmunoassay can be employed. A PAR receptor can be assessed by a radioimmunoassay by first obtaining a suitable sample to be tested. The sample is contacted with an anti-PAR antibody (e.g., an anti-PAR antibody comprising a radioactive label, or an anti-PAR antibody comprising a binding site for a second antibody that has a radioactive label) preferably in an amount in excess of that required to bind the PAR receptors expressed on the platelets, and under conditions suitable for the formation of labeled complexes between the anti-PAR antibody and activated platelets. The formation of the complex in the samples is determined by detecting or measuring the radioactivity in the sample.

Enzyme-Linked Immunosorbent Assays (ELISA):

Detection of a PAR receptor in a suitable sample can also occur by employing ELISA methods. To determine a measurement of a PAR receptor using an ELISA assay in a suitable sample, one contacts the sample with an anti-PAR antibody, and then measures the formation of a complex between the anti-PAR antibody and the PAR receptor(s) in the sample. The PAR receptor(s) can be measured by direct, indirect, sandwich or competitive ELISA formats. An antibody can be conjugated with labels such as biotin and HRP-streptavidin.

A solid support, such as a microtiter plate, dipstick, bead, or other suitable support, can be coated directly or indirectly with an anti-PAR antibody. For example, an anti-PAR antibody can coat a microtiter well, or a biotinylated anti-PAR MoAbs can be added to a streptavidin coated support. A variety of immobilizing or coating methods as well as a number of solid supports can be used, and can be selected according to the desired format.

In one embodiment, the sample or PAR receptor standard is combined with the solid support simultaneously with the detector antibody. Optionally, this composition can be combined with a one or more reagents by which detection is monitored. For example, the sample such as PPP can be combined with the solid support simultaneously with (a) HRP-conjugated anti-PAR MoAbs, or (b) a biotinylated anti-PAR MoAbs and HRP-streptavidin.

A known amount of the PAR receptor standard can be prepared and processed as described above for a suitable sample. This PAR receptor standard assists in quantifying the amount of PAR receptors detected by comparing the level of PAR receptors in the sample relative to that in the standard.

A physician, technician, apparatus or a qualified person can compare the amount of detected complex with a suitable control to determine if the levels are decreased. For example, the level of a PAR receptor following a vascular intervention procedure can be compared with a basal level for the individual, such as a level determined prior to or at the time of the procedure, or with levels in normal individuals or suitable controls, as described herein.

A variety of methods can determine the amount of PAR receptors in complexes. For example, when HRP is used as a label, a suitable substrate such as OPD can be added to produce color intensity directly proportional to the bound anti-PAR MoAbs (assessed e.g., by optical density), and therefore to the PAR receptors in the sample. One can compare the results to a suitable control such as a standard, levels of PAR receptors in normal individuals, and baseline levels of PAR receptors in a sample from the same donor. For example, the assay can be performed using a known amount of a PAR receptor standard in lieu of a sample, and a standard curve established. One can relatively compare known amounts of the a PAR receptor standard to the amount of complex formed or detected.

PAR-1 and/or PAR-4 levels can be assessed using methods that are currently known in the art, as well as those that are later discovered.

Modes and Manner of Administration, Dosages

The statins used in the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17$^{th}$ Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include, potassium sorbate, sodium metabisulfite, methyl paraben, propyl paraben, thimerosal, etc. The compositions can also be combined where desired with other active substances, e.g., enzyme inhibitors, to reduce metabolic degradation. A carrier (e.g., a pharmaceutically acceptable carrier) is preferred, but not necessary to administer the compound.

The statin can be a liquid solution, suspension, emulsion, tablet, pill, capsule, sustained release formulation, or powder. The method of administration can dictate how the composition will be formulated. For example, the composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The statins used in the invention can be administered intravenously, parenterally, intramuscular, subcutaneously, orally, nasally, topically, by inhalation, by implant, by injection, or by suppository. The composition can be administered in a single dose or in more than one dose over a period of time to confer the desired effect. In one embodiment, atorvastatin, pravastatin, fluvastatin, cerivastatin, lovastatin, simvastatin, rosuvastatin, or pitavastatin, can be administered orally in an amount between about 2 mg-100 mg/daily (e.g., 10, 20, 40 or 80 mg/daily).

The actual effective amounts of compound or drug can vary according to the specific composition being utilized, the mode of administration and the age, weight and condition of the patient. For example, as used herein, an effective amount of the drug is an amount which reduces the platelet activation state. Dosages for a particular individual patient can be determined by one of ordinary skill in the art using conventional considerations, (e.g. by means of an appropriate, conventional pharmacological protocol).

For enteral or mucosal application (including via oral and nasal mucosa), particularly suitable are tablets, liquids, drops, suppositories or capsules. A syrup, elixir or the like can be used wherein a sweetened vehicle is employed. Liposomes, microspheres, and microcapsules are available and can be used.

Pulmonary administration can be accomplished, for example, using any of various delivery devices known in the art such as an inhaler. See. e.g., S. P. Newman (1984) in *Aerosols and the Lung*, Clarke and Davis (eds.), Butterworths, London, England, pp. 197-224; PCT Publication No. WO 92/16192; PCT Publication No. WO 91/08760.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

The administration of the statin and the vascular treating compound can occur simultaneously or sequentially in time. The vascular treating compound can be administered before, after or at the same time as the statin. Thus, the term "co-administration" is used herein to mean that the statin and the vascular treating compound will be administered at times to achieve a reduction or treatment of the vascular event or disease, and inhibition of PAR-1 or PAR-4. The methods of the present invention are not limited to the sequence in which the statin and vascular treating compound are administered, so long as the vascular treating compound is administered close enough in time to produce the desired effect of reducing the platelet activation state.

A description of preferred embodiments of the invention follows.

EXEMPLIFICATION

Statins Inhibit PAR-1 And PAR-4

Methods:

Patients:

The study was designed as a prospective, single blinded, placebo controlled trial of 6 major statins currently available in the US. The study was approved by local institutional review boards. Written informed consent was obtained from all patients, who were informed of the strict compliance rules, and compensated for outpatient visits, and blood draws. Patients aged $\geq 21$ years were eligible if they had a documented evidence of coronary artery disease (proved by coronary angiography).

Patients were excluded for a history of bleeding diathesis, drug or alcohol abuse, prothrombin time greater than 1.5 times control, platelet count <100,000/mm3, hematocrit <25%, or creatinine >4.0 mg/dl, surgery or angioplasty for symptomatic stenosis performed within 3 months or planned for the future, known allergy to aspirin, clopidogrel, or statins, history of gastrointestinal or other bleeding, history of drug-induced disorders, trauma or surgery within the last 3 months, any surgery planned for the next 3 months, cancer, rheumatic diseases, or seizures. Patients participating in other investigational drug trials within one month of completion were also excluded. No patients had previously received intravenous platelet glycoprotein IIb/IIIa inhibitors for the last 6 months.

Samples

Blood samples were obtained with a 19-gauge needle by direct venipuncture and drawn into two 7-ml vacutainer tubes at room temperature containing 3.8% trisodium citrate. The vacutainer tube was filled to capacity and gently inverted 3 to 5 times to ensure complete mixing of the anticoagulant. The first 4-5 ml of blood were used for lipid profile analysis, or discharged. All samples were labeled with coded number and analyzed by blinded technicians. Platelet studies were performed at baseline as well as at Week 4, and Week 6.

Measuring PAR-1/PAR-4 Receptors by Whole Blood Flow Cytometry

The blood-citrate mixture (50 μl) was diluted with 450 μl Tris buffered saline (TBS) (10 mmol/l Tris, 0.15 mol/l sodium chloride) and mixed by inverting an Eppendorf tube gently two times. The appropriate antibody was then added (5 μl) and incubated at 37° C. for 30 minutes, After incubation, 400 μl of 2% buffered paraformaldehyde was added for fixation. The samples were analyzed on the FACScan flow cytometer (Becton Dickinson, San Diego, Calif.) calibrated to measure fluorescent light scatter. All parameters were collected using four-decade logarithmic amplification. The data were collected in list mode files and then analyzed. The surface expression of platelet receptors was determined by flow cytometry using the following monoclonal antibodies: cleaved (WEDE15), and intact (SPAN12) platelet thrombin PAR-1/PAR-4 receptors (Beckman Coulter, Brea, Calif.), and they were expressed as log mean fluorescence intensity.

Statistical Analysis

The significance of differences between treatments arms was calculated by c2 and Fisher's exact tests for discrete variables, and Wilcoxon rank-sum test for continuous variables. The significance of differences between individual flow cytometric histograms was calculated using the Smirnov-Kolgomorov test incorporated in the CELLQuest' (San Diego, Calif.) software. Statistical analyses were performed using SPSS/E11.5 (SPSS, Inc., Chicago, Ill.). To control for any baseline differences analysis of variance was used. All p values are 2 sided.

Results

Patients:

Seventy patients were screened in, assigned, and completed the six weeks study. There were no deaths, serious adverse events, or hospitalizations. Table 1 shows baseline pretreatment distribution of demographics, risk factors, clinical characteristics, and concomitant medications in 6 statin-, and one control arms. There were no significant differences between the groups, and concomitant medications were used fairly even.

TABLE 1

| | Baseline Clinical Characteristics of Patients with Coronary Artery Disease | | | | | | |
|---|---|---|---|---|---|---|---|
| Variable | No statins (n = 10) | Atorvastatin (n = 10) | Rosuvastatin (n = 10) | Pravastatin (n = 10) | Simvastatin (n = 10) | Fluvastatin (n = 10) | Lovastatin (n = 10) |
| Age, yrs ± SD | 61.8 ± 7.0 | 64.2 ± 10.1 | 62.5 ± 7.7 | 65.5 ± 6.4 | 58.3 ± 9.1 | 57.9 ± 11.0 | 65.2 ± 6.8 |
| Gender, n (% male) | 8 (60%) | 8 (80%) | 6 (60%) | 6 (60%) | 8 (80%) | 7 (70%) | 6 (60%) |
| | | | Race, n (%) | | | | |
| Caucasian | 7 (70%) | 9 (90%) | 6 (60%) | 8 (80%) | 8 (80%) | 8 (80%) | 7 (70%) |
| African-American | 3 (30%) | — | 4 (40%) | 2 (20%) | 1 (10%) | 1 (10%) | — |
| Asians | — | 1 (10%) | — | — | 1 (10%) | 1 (10%) | 3 (30%) |
| | | | Primary Diagnosis, n (%) | | | | |
| Stable angina | 9 (90%) | 8 (80%) | 7 (70%) | 10 (100%) | 8 (80%) | 9 (90%) | 8 (80%) |
| Unstable angina | 1 (10%) | 1 (10%) | 1 (10%) | — | — | — | 2 (20%) |
| Other | — | 1 (10%) | 2 (20%) | — | 2 (20%) | 1 (10%) | — |
| | | | Risk factors | | | | |
| Total cholesterol, ± SD | 244 ± 52 | 275 ± 33 | 301 ± 59 | 282 ± 39 | 197 ± 25 | 261 ± 30 | 274 ± 42 |
| Triglycerides, ± SD | 155 ± 61 | 168 ± 57 | 174 ± 52 | 160 ± 41 | 148 ± 55 | 180 ± 58 | 161 ± 50 |

TABLE 1-continued

Baseline Clinical Characteristics of Patients with Coronary Artery Disease

| Variable | No statins (n = 10) | Atorvastatin (n = 10) | Rosuvastatin (n = 10) | Pravastatin (n = 10) | Simvastatin (n = 10) | Fluvastatin (n = 10) | Lovastatin (n = 10) |
|---|---|---|---|---|---|---|---|
| HDL-C, ± SD | 37 ± 11 | 40 ± 10 | 36 ± 7 | 41 ± 9 | 38 ± 8 | 35 ± 6 | 37 ± 6 |
| LDL-C, ± SD | 127 ± 48 | 130 ± 39 | 135 ± 34 | 142 ± 30 | 140 ± 43 | 129 ± 30 | 135 ± 38 |
| Tobacco use, n (%) | 5 (50%) | 4 (40%) | 4 (40%) | 6 (60%) | 3 (30%) | 5 (50%) | 4 (40%) |
| Hypertension, n (%) | 8 (80%) | 9 (90%) | 9 (90%) | 8 (80%) | 7 (70%) | 7 (70%) | 7 (70%) |
| Diabetes, n (%) | 4 (40%) | 4 (40%) | 6 (60%) | 6 (60%) | 5 (50%) | 3 (30%) | 5 (50%) |
| Medical History, n (%) | | | | | | | |
| Previous MI | — | — | — | 1 (10%) | 2 (20%) | — | — |
| Heart Failure | 1 (10%) | — | — | 1 (10%) | 1 (10%) | 1 (10%) | 2 (20%) |
| Peripheral vascular disease | 3 (30%) | 3 (30%) | 2 (20%) | 2 (20%) | 3 (30%) | 2 (20%) | 2 (20%) |
| Heart surgery | 1 (10%) | — | — | 2 (20%) | 1 (10%) | — | — |
| Medications, n (%) | | | | | | | |
| Beta-blockers | 6 (60%) | 6 (60%) | 4 (40%) | 4 (40%) | 7 (70%) | 7 (70%) | 5 (50%) |
| ACE inhibitors | 3 (30%) | 2 (20%) | 3 (30%) | 2 (20%) | 1 (10%) | 3 (30%) | 3 (30%) |
| Ca-channel blockers | 1 (10%) | 1 (10%) | 2 (20%) | 3 (30%) | 2 (20%) | 2 (20%) | — |
| AT-receptor antagonists | 4 (40%) | 4 (40%) | 5 (50%) | 3 (30%) | 5 (50%) | 4 (40%) | 5 (50%) |
| Antidepressants | 3 (30%) | 2 (20%) | 3 (30%) | 4 (40%) | 4 (40%) | 2 (20%) | 1 (10%) |
| Aspirin | 8 (80%) | 10 (100%) | 10 (100%) | 9 (90%) | 10 (100%) | 10 (100%) | 9 (90%) |
| Clopidogrel | 3 (30%) | 4 (40%) | 3 (30%) | 3 (30%) | 5 (50%) | 4 (40%) | 2 (20%) |
| Warfarin | 1 (10%) | — | — | 1 (10%) | 1 (10%) | — | — |

Statin Doses:

Patients were assigned to 6 major statins, or serve as a control group with no statin therapy. The brand, and dose of statin was at physician discretion. Patients were assigned in each study arm until the cell is filled. Table 2 exhibit the frequency of different statin doses used in the index study PAR-1/PAR-4 Expression:

PAR-1 is a member of a novel gene family of G-protein couples receptors. PAR-1 is a single polypeptide of 66 kDa with a thrombin cleavage site located near the extracellular N terminus. This receptor is expressed by human platelets and is responsible for attracting alpha-thrombin to the platelet surface. The SPAN12 monoclonal antibody used in this study specifically reacts with PAR-1. It was found that a consistent and significant reduction of PAR-1 platelet expression in the statin treated patients independently of the brand of statin used.

More specifically, the data on PAR-1/PAR-4 thrombin receptor expression in all groups are presented in Table 3. At baseline, there was no difference in receptor expression. However, 4 weeks of treatment with statins resulted in a significant inhibition of the activated epitope of PAR-1/PAR-4 platelet expression as measured by WEDE-15 monoclonal antibody. There was a slight rebound at week 6, but still significant inhibition was observed. The pattern of inhibition of non-activated intact epitope (measured with SPAN-12 antibody) was delayed. For most groups it takes six weeks (with the exception of simvastatin and pravastatin) of therapy to develop the inhibition of the intact receptor.

TABLE 2

Doses of statins used in the platelet PAR-1/PAR-4 studies.

| Statin Daily Dose | Atorvastatin (n = 10) | Rosuvastatin (n = 10) | Pravastatin (n = 10) | Simvastatin (n = 10) | Fluvastatin (n = 10) | Lovastatin (n = 10) |
|---|---|---|---|---|---|---|
| 5 mg | N/A | 1 (10%) | N/A | 0 | N/A | N/A |
| 10 mg | 2 (20%) | 7 (70%) | 2 (20%) | 2 (20%) | N/A | 5 (50%) |
| 20 mg | 4 (40%) | 2 (20%) | 7 (70%) | 3 (30%) | 2 (20%) | 4 (40%) |
| 40 mg | 4 (40%) | 0 | 1 (10%) | 4 (40%) | 6 (60%) | 1 (10%) |
| 80 mg | 0 | N/A | N/A | 1 (10%) | 2 (20%) | N/A |

TABLE 3

Effects of Statins on the Platelet PAR-1/PAR-4 receptors Patients with Coronary Artery Disease

| Variable | No statins (n = 10) | Atorvastatin (n = 10) | Rosuvastatin (n = 10) | Pravastatin (n = 10) | Simvastatin (n = 10) | Fluvastatin (n = 10) | Lovastatin (n = 10) |
|---|---|---|---|---|---|---|---|
| WEDE15-MoAbs (activated, cleaved epitope of (PAR-1/PAR-4 receptors) | | | | | | | |
| Baseline | 24.4 ± 5.4 | 27.5 ± 4.9 | 30.1 ± 7.2 | 28.2 ± 4.4 | 29.0 ± 7.3 | 27.1 ± 5.9 | 26.8 ± 4.9 |
| Week 4 | 27.1 ± 6.1 | 16.1 ± 5.8* | 17.4 ± 5.5* | 16.9 ± 4.8* | 16.6 ± 5.5* | 18.0 ± 5.8* | 18.4 ± 5.0* |
| Week 6 | 25.0 ± 8.3 | 18.0 ± 7.4* | 22.6 ± 7.2* | 20.1 ± 6.6* | 23.4 ± 8.1 | 20.7 ± 4.1* | 23.0 ± 6.3 |

TABLE 3-continued

Effects of Statins on the Platelet PAR-1/PAR-4 receptors Patients with Coronary Artery Disease

| Variable | No statins (n = 10) | Atorvastatin (n = 10) | Rosuvastatin (n = 10) | Pravastatin (n = 10) | Simvastatin (n = 10) | Fluvastatin (n = 10) | Lovastatin (n = 10) |
|---|---|---|---|---|---|---|---|
| | | | SPAN-12-MoAbs (nonactive, intact epitope of PAR-1/PAR-4 receptors) | | | | |
| Baseline | 43.6 ± 5.8 | 46.1 ± 8.3 | 42.2 ± 9.4 | 50.3 ± 9.1 | 45.4 ± 7.0 | 42.8 ± 8.2 | 40.6 ± 6.9 |
| Week 4 | 40.4 ± 6.0 | 39.5 ± 5.7 | 33.6 ± 5.9 | 29.0 ± 6.7* | 26.5 ± 5.8* | 37.1 ± 7.3 | 40.0 ± 8.1 |
| Week 6 | 50.7 ± 5.2 | 30.8 ± 4.0* | 25.1 ± 7.0* | 32.6 ± 8.4* | 24.9 ± 6.2* | 29.9 ± 6.4* | 31.1 ± 5.5* |

Receptor expression is presented as Log mean fluorescence intensity;
*$p < 0.05$ The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details can be made therein without departing from the scope of the invention encompassed by the appended claims.

What is claimed is:

1. A method of treating a myocardial infarction associated with increased PAR-1, PAR-4 or both in an individual, wherein the method comprising:

a) selecting an individual diagnosed with vascular disorder characterized by having an elevated G-coupled Protease Activating Receptor (PAR)-1 level, an elevated PAR-4 level, or both;

b) administering to said individual an amount of an atorvastatin, wherein the atorvastatin is administered in an amount between 5 mg and 250 mg to thereby inhibit PAR-1, PAR-4 or both; and c) detecting in said individual the level of PAR-1, PAR-4 or both and comparing said level to step a);

wherein the atorvastatin reduces the PAR-1 level, the PAR-4 level or both, as compared to the level prior to step b), to thereby treat the vascular disorder.

* * * * *